United States Patent
Koning et al.

(10) Patent No.: US 6,480,370 B1
(45) Date of Patent: Nov. 12, 2002

(54) POLYMERIC DIELECTRIC MATERIAL FOR HIGH-ENERGY DENSITY CAPACITORS

(75) Inventors: Paul A. Koning, Chandler, AZ (US); Paul H. Wermer, San Francisco, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 09/473,171

(22) Filed: Dec. 28, 1999

(51) Int. Cl.[7] .................................................. H01G 4/06
(52) U.S. Cl. ..................... 361/321.2; 361/528; 361/529; 361/532; 257/40
(58) Field of Search .............................. 361/321.2, 525, 361/528, 529, 523, 526, 509, 524, 516, 532; 257/40

(56) References Cited

U.S. PATENT DOCUMENTS

| | | | |
|---|---|---|---|
| 4,490,774 A | * 12/1984 | Olson et al. ................ 361/311 |
| 4,668,349 A | * 5/1987 | Cuellar et al. ................ 204/59 |
| 4,879,064 A | * 11/1989 | Adkins ....................... 252/500 |
| 5,250,378 A | 10/1993 | Wang ........................... 430/83 |
| 5,280,183 A | * 1/1994 | Batzel et al. .................. 257/40 |
| 5,281,616 A | * 1/1994 | Dixon et al. ................. 514/410 |
| 5,436,796 A | * 7/1995 | Abe et al. .................... 361/525 |
| 5,472,900 A | 12/1995 | Vu et al. ....................... 437/60 |
| 5,665,490 A | * 9/1997 | Takeuchi et al. ............. 429/192 |
| 5,698,339 A | 12/1997 | Kawakami et al. ......... 429/212 |
| 5,798,556 A | * 8/1998 | Hughes et al. .............. 257/414 |
| 5,840,443 A | 11/1998 | Gregg et al. ................ 429/212 |
| 5,842,626 A | 12/1998 | Bhansali et al. ....... 228/180.22 |
| 5,912,809 A | 6/1999 | Steigerwald et al. ........ 361/780 |
| 5,925,562 A | 7/1999 | Nova et al. ............. 435/287.1 |
| 5,965,202 A | 10/1999 | Taylor-Smith et al. ...... 427/245 |
| 5,965,273 A | 10/1999 | Walpita et al. ............. 428/457 |
| 5,973,908 A | 10/1999 | Saia et al. .................. 361/311 |
| 6,134,099 A | * 10/2000 | Igaki et al. ................. 361/509 |

* cited by examiner

*Primary Examiner*—Dean A. Reichard
*Assistant Examiner*—Nguyen Ha
(74) *Attorney, Agent, or Firm*—Schwegmen, Lundberg, Woessner & Kluth, P.A.

(57) ABSTRACT

The present invention includes a dielectric. The dielectric comprises a polymer that has a high dielectric constant. The polymer comprises polarizable species. The present invention also includes an embedded capacitor, and an IC package made with the dielectric.

15 Claims, 8 Drawing Sheets

POLYMERIC DIELECTRIC MATERIAL FOR HIGH-ENERGY DENSITY CAPACITORS

BACKGROUND OF THE INVENTION

The present invention relates to a polymeric dielectric material for use in high-energy density capacitors, a high-energy density capacitor made with the polymeric dielectric material and an integrated circuit package that comprises a high energy capacitor made with the polymeric material of the present invention.

Multiple layer printed circuit boards (PCBs) are used in computer systems for interconnecting integrated circuit (IC) chips and other electronic components and devices. A multiple layered printed circuit board is formed from a substrate supporting a plurality of insulated conductive trace layers. The insulated trace layers typically include surface conductive trace layers and embedded trace layers with selected trace layers connected as a ground plane and a power plane. Integrated circuits and electronic components and devices are mounted on an outer surface of the multiple layered printed circuit board by a variety of well-known techniques.

One problem arising with multiple layered printed circuit boards is that electronic operation of integrated circuits includes switching that results in high frequency fluctuations in the potential difference between the power plane and the ground plane. This problem has been addressed using bypass capacitors connected between the power plane and the ground plane and mounted in the general vicinity of each integrated circuit. As used herein, the term "bypass capacitor" is equivalent to the term "power conditioning capacitor." The bypass capacitors are generally effective in reducing and stabilizing voltage fluctuations for low frequency voltage oscillations. Unfortunately, a via connection of a bypass capacitor to the power and ground planes introduces a small inductance that impedes the bypass function of a bypass capacitor and reduces the effectiveness of the bypass capacitor to stabilize voltage fluctuations at higher frequencies.

Types of power conditioning capacitor devices fabricated in printed circuit boards include surface mounted power conditioning capacitors and embedded power conditioning capacitors. A surface mounted power conditioning capacitor is typically mounted in conjunction with printed circuit board embodiments. The surface mounted power conditioning capacitor is positioned as closely as possible to the chip it protects.

Surface mounted power conditioning capacitors, such as is shown in one prior art embodiment at 20 in FIG. 4, have several problems as compared to embedded capacitors, one embodiment of which is illustrated at 30 in FIG. 3. One problem is that large numbers of surface power conditioning capacitors are needed to accommodate the current requirements and to reduce circuit noise. Also, surface power conditioning capacitors have resistance and inductance limitations, occupy considerable surface space, increase the number of solder joints and, therefore, reduce the system reliability.

Materials with high dielectric constants and low loss tangents have had use in solving these problems and in fabricating capacitors. Several high dielectric constant materials based upon polymers combined with ceramics are known. U.S. Pat. Nos. 4,335,180 and 5,358,775, owned by Rogers Corporation, describe composites of fluoropolymers, such as polytetrafluoroethylene, PTFE, and ceramics that have a high dielectric constant.

A high dielectric composite that comprises a matrix polymer wherein the matrix polymer includes an epoxy resin based on bisphenol F epoxy and an organic amino curing agent was described by S. Asai, et al., in *IEEE Transactions on Components, Hybrids and Manufacturing Technology*, vol. 16, No. 5, August, 1993. The polymer, which has a high dielectric constant, also includes a barium titanate filler at a 34 volume percent level.

NEC has produced a high energy density capacitor which is based on a carbon/sulfuric acid dielectric. The NEC device has a high capacitance that drops off rapidly with frequency.

These polymeric and ceramic-based materials generally have a problem with temperature stability. The dielectric constants of these high dielectric ceramic-based materials change with temperature. The change in dielectric constant changes the electrical properties of a component such as a capacitor.

SUMMARY OF THE INVENTION

One embodiment of the present invention includes a dielectric. The dielectric comprises a polymer that has a high dielectric constant and that comprises a polarizable species.

Another embodiment of the present invention includes a laminate comprising the dielectric of the present invention. The laminate comprises a flat substrate with two surfaces, comprising the dielectric of the present invention and a layer of conducting material adhering to at least one of the two surfaces of the substrate.

Another embodiment of the present invention includes an embedded capacitor. The embedded capacitor comprises a dielectric with a high dielectric constant. The dielectric includes a polymer with polarizable species.

One other embodiment of the present invention includes an embedded capacitor assembly. The embedded capacitor assembly comprises at least about one pair of vias and a capacitor that comprises a dielectric with a high dielectric constant. The dielectric comprises a polymer that has at least one polarizable species.

Another embodiment of the present invention includes a printed circuit board that comprises an IC package that has a high capacitance. The printed circuit board includes the IC package that comprises a capacitor that comprises a polymer. The polymer has a high dielectric constant. The polymer comprises a polarizable species.

One other embodiment includes a method of making a laminate of the present invention. The method includes providing a dielectric of the present invention and shaping the dielectric into a flat substrate. A conductor is applied to one or both of two surfaces of the flat substrate.

DETAILED DESCRIPTION

Terminology

The terms "chip," "integrated circuit," "monolithic device," "semiconductor device" and "microelectronic device" are often used interchangeably in this field. The present invention is applicable to all of the above as they are generally understood in the field.

The terms "metal line," "trace," "wire," "conductor," "signal path" and "signaling medium" are all related. The related terms listed above, are generally interchangeable, and appear in order from specific to general. In this field, metal lines are sometimes referred to as traces, wires, lines, interconnect or simply metal. Metal lines, such as aluminum, copper, an alloy of aluminum and copper, an alloy of aluminum, copper and silicon, an alloy of copper and magnesium, or an alloy of copper and niobium are conductors that provide signal paths for coupling or interconnecting electrical circuitry. Conductors other than metal are available in microelectronic devices. Materials such as doped polysilicon, doped single-crystal silicon, regardless of whether such doping is achieved by thermal diffusion or ion implantation, titanium, and refractory metal suicides are examples of other conductors.

The terms "contact" and "via" both refer to structures for electrical connection of conductors from different interconnect levels. These terms are sometimes used in the art to describe both an opening in an insulator in which the structure will be completed, and the completed structure itself. For purposes of this disclosure, contact and via refer to the completed structure.

The expression, "low dielectric constant material", refers to materials having a lower dielectric constant than oxides of silicon. Most organic polymers and silicon-based insulators containing organic polymers typically have lower dielectric constants than silicon dioxide.

The expression "high dielectric constant material", refers to materials having a dielectric constant greater than oxides of silicon. For some embodiments, the dielectric constant is about 750 to 1000.

The term "vertical," as used herein, means substantially orthogonal to the surface of a substrate.

Overview

Figure 4:
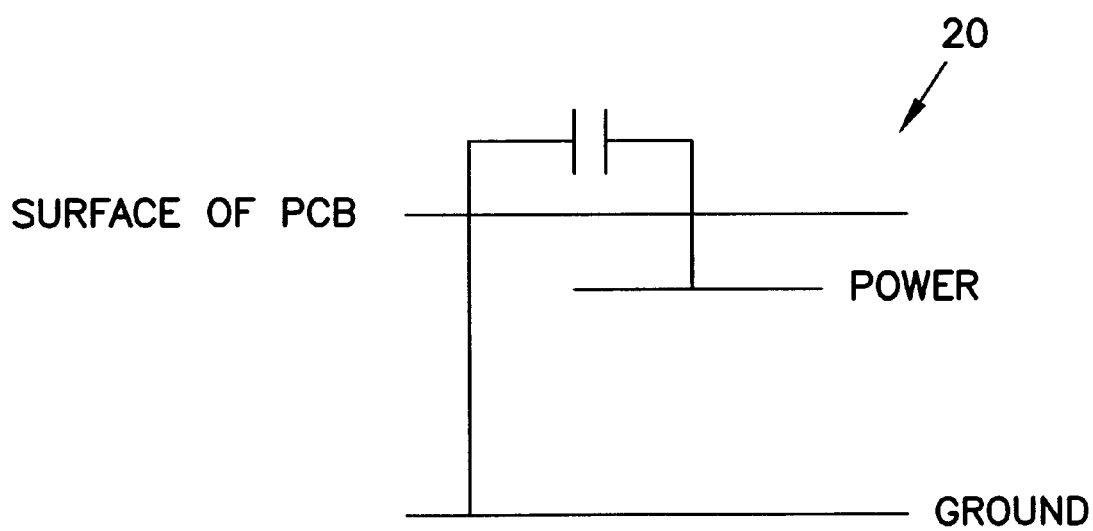
FIG. 4 illustrates a schematic view of a prior art discrete capacitor on a surface of PCB.

The polymer dielectrics of the present invention are usable in production of both discrete capacitors, such as is illustrated at 20 in FIG. 4 and integral capacitors for printed circuit board (PCB) applications. The polymer dielectrics are characterized by having high dielectric constants and by comprising easily polarizable chemical species. The polymer dielectrics of the present invention comprise a polymeric structure and a metal ion held within the polymeric structure by physical and chemical bonds. The polymeric structure bonds the metal ion so as to restrict motion in an x—y plane while permitting greater motion in an x—z or y—z plane. This differential metal ion movement, greater relative movement in the x—z and y—z planes, as well as a lack of gross long range ion motion, give rise to a high dielectric constant for the polymer dielectrics of the present invention. The dielectric constants are about 100 for some embodiments. It is contemplated that for other embodiments, the dielectric constants are as high as about 750 to 1000.

Examples of polymer dielectrics of the present invention include metal ion free dielectrics such as polymer bound organic acids and salts of the acids, such as carboxylic acids, aromatic sulfonic acids, and phosphate esters. The polymer dielectrics also include metal containing dielectrics and complex cation containing dielectrics such as aromatic amines, cyclic polyamines, or aliphatic quaternary amines, polymer bound chelating agents containing protons and/or metal ions, such as cyclic polyethers, crown ethers or metal complexes of crown ethers, porphyrin rings that are either free base or metallo derivatives, and ethylenediaminetetraacetic acid (EDTA) or metallo derivatives of EDTA.

Figure 1A:
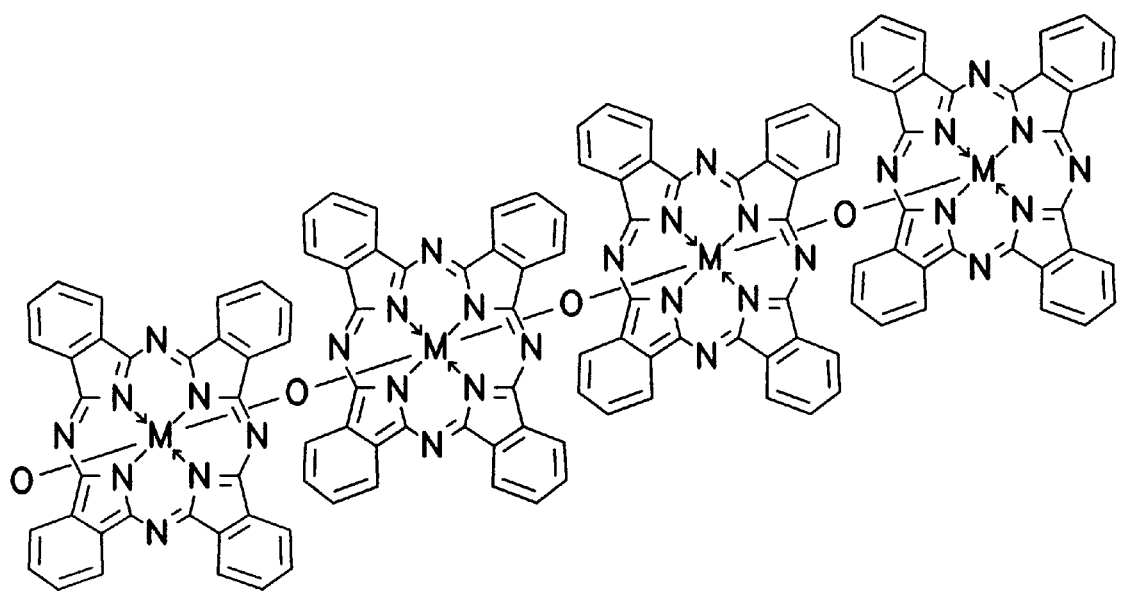
FIG. 1A illustrates a schematic view of a polymer that comprises a main chain and side chain porphyrin ring such as a metallophthalocyanine.
Figure 1B:
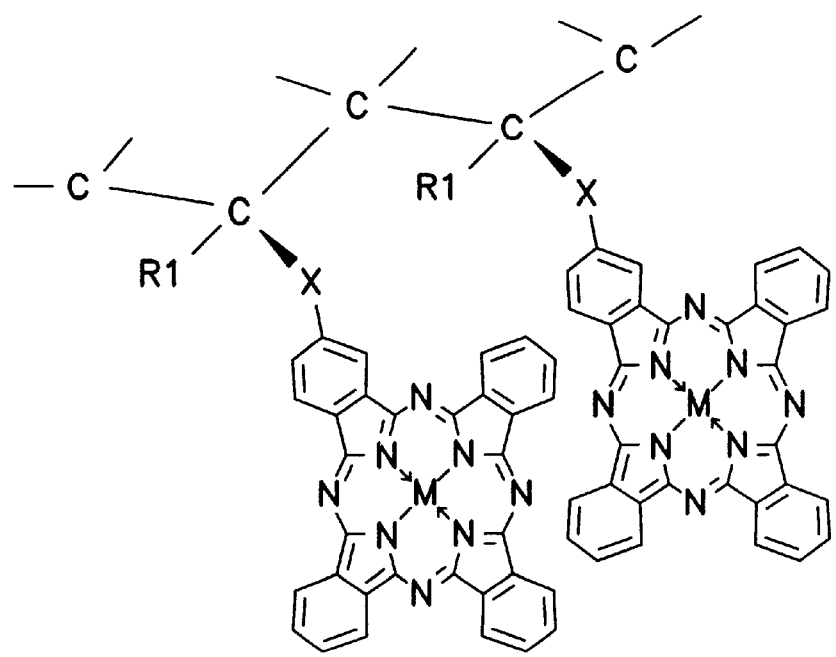
FIG. 1B illustrates a schematic view of a metallophthalocyanine attached to a side group of a polymer chain such as polymethylmethacrylate.

One example of a compound with a porphyrin ring system that comprises a main chain and a side chain, is a metallophthalocyanine, illustrated generally in FIG. 1A. The compound in FIG. 1A illustrates a main chain that is formed by linking metallophthalocyanine units with oxygen atoms. FIG. 1B illustrates a metallophthalocyanine that is attached to a side group of a polymer chain such as polymethylmethacrylate.

Figure 2:
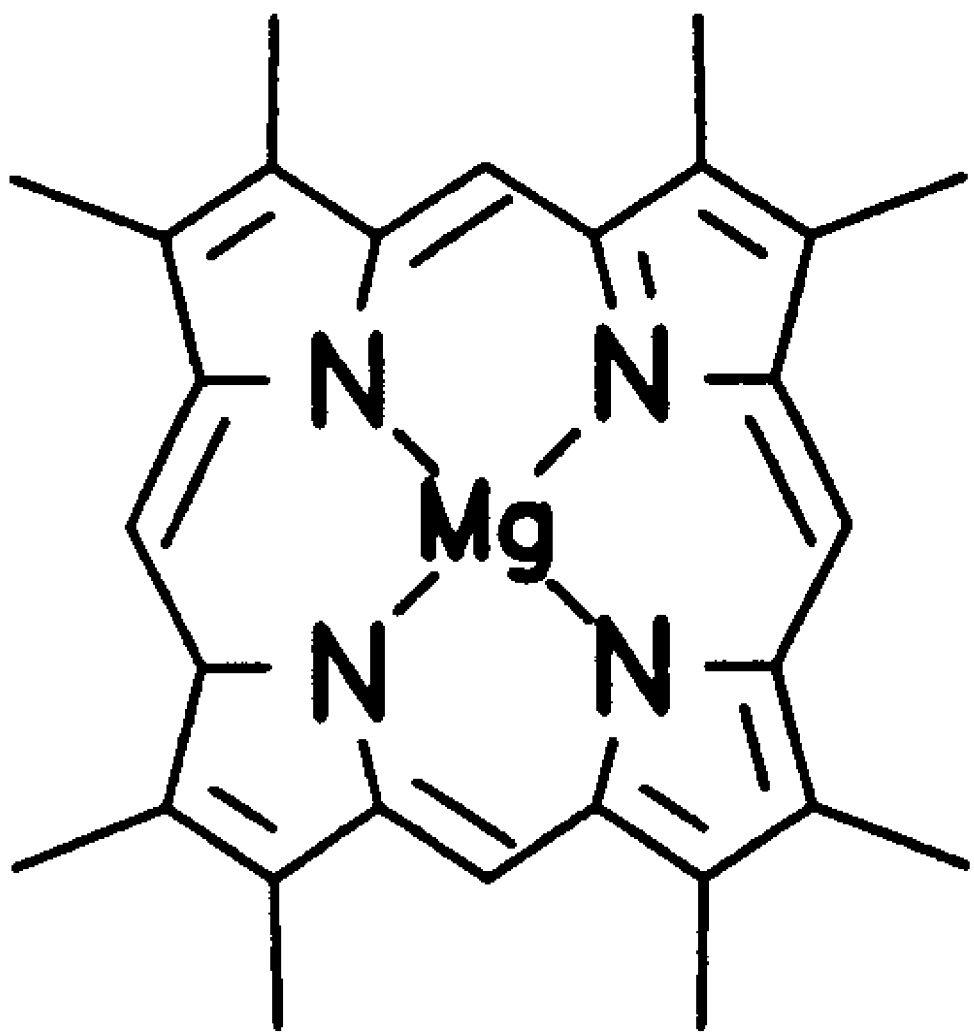
FIG. 2 illustrates a representational view of a monomeric porphyrin ring with a magnesium atom chelated in the center of the ring.

A monomeric porphyrin ring with a magnesium atom chelated in the center of the ring is shown in FIG. 2. While a magnesium chelated porphyrin is shown, iron chelated porphyrin ring systems and copper chelated porphyrin ring systems are also usable as dielectrics in embodiments of the present invention. For these and other embodiments, the metal ion is a cation with a high charge density that can be complexed by the porphyrin complex. The porphyrin ring systems, for some embodiments, comprise side chains such as phytol side chains.

The polymer dielectrics of the present invention further include polymer bound organometallic complexes such as metallocene. Specific metallocenes include ferrocene, cobaltocene and ruthenocene. The dielectric polymers additionally include metal ions or metal clusters trapped in carbon buckyball or nanotube structures.

The polymer dielectrics of the present invention are a substantial improvement over high dielectric ceramics and polymer/ceramic blends. High dielectric ceramics require a high temperature firing. The polymer dielectrics of the present invention do not require a high temperature firing. Ceramic blends are limited in flexibility because of the particulate-based structure. Particles limit flexibility by limiting the thinness of the structure.

The polymer dielectrics are not particulate-based. As a consequence, the lower film thicknesses are not limited by the size of the particulate filler and thinner structures are possible to fabricate as compared to ceramic blend structures. The thinner structure imparts a more flexible capacitor structure with the polymer dielectric as compared to using a ceramic or a polymer/ceramic blend dielectric.

Furthermore, high dielectric ceramics such as ferroelectric or perovskite ceramics derive their electrical properties from metal ions which are fixed in a metal oxide lattice. Examples of ferroelectric ceramics include $PbTiO_2$, $BaTiO_2$ and $PbZrO_3$. In these oxide structures, it is the polarizability of the Pb and Ba and charge displacement of the Ti that give rise to the desired property. These metal atoms are allowed slight movement in the oxide lattice, but not large scale ion migration. It is believed that strongly chelating metal ions in a polymer matrix of the dielectric of the present invention approach the polarizability and limited mobility of ions found in the ceramics. This is because of the greater freedom of movement in the x—z and the y—z planes as compared to the x—y plane.

The dielectrics of the present invention bind a polymeric ion more tightly than sulfuric acid absorbed onto carbon. However, the dielectrics do not bind a metal ion so tightly that the ion has substantially no movement. It is believed that this results in an improvement in the frequency of the capacitor.

The application viscosity of the polymer dielectric of the present invention is very amenable to standard PCB processing techniques, such as spin, spraying or curtain coating, and vacuum lamination. The polymer dielectrics are also a closer CTE match to the PCB than the ceramic dielectrics. Specific process parameters such as production rate, spin-time, deposition temperature, formulation viscosity and so on are within the capabilities of those having ordinary skill in the art. For instance, one process embodiment includes spin coating or dip coating a solution containing a metallic porphyrin and a material such as poly(ethyleneglycol) diglycidylether.

The polymer dielectrics of the present invention have a low gas permeability and moisture absorption, a low coefficient of thermal expansion and a high tensile modulus, particularly if employed in conjunction with nanotubes or buckyballs, also known herein as Buckminister fullerenes. When the dielectrics are employed in conjunction with Buckminster fullerenes, or ion exchange particles, a greater quantity of the dielectric is spatially positioned because of the high microporosity of the fullerenes or ion exchange particles. A Buckminster fullerene exhibits a porous caged structure and imparts this structure to the dielectric.

The fullerene, nanotube and ion exchange particle embodiments of the dielectric of the present invention are made by incorporating the polymers described herein. Thus, for these embodiments, the pore size of the dielectric product is determined by the pore size of the buckminster-fullerene or nanotube or ion exchange particles.

The polymer dielectrics of the present invention are shapable to form articles such as films, sheets, plaques, disks, and other flat shapes which are particularly useful as substrates in electronics, such as printed circuit boards. Laminates having a high dielectric constant are also readily made with the dielectrics of the present invention. The laminates comprise a flat substrate of the dielectric polymer, such as a sheet, film or plaque, placed between two layers of a metal such as copper. The metal is not necessary applied by a lamination process, so that the term "laminates" has a broader meaning and includes multilayer structures made by methods other than lamination. The flat substrates have two surfaces, other than edges.

Figure 3:
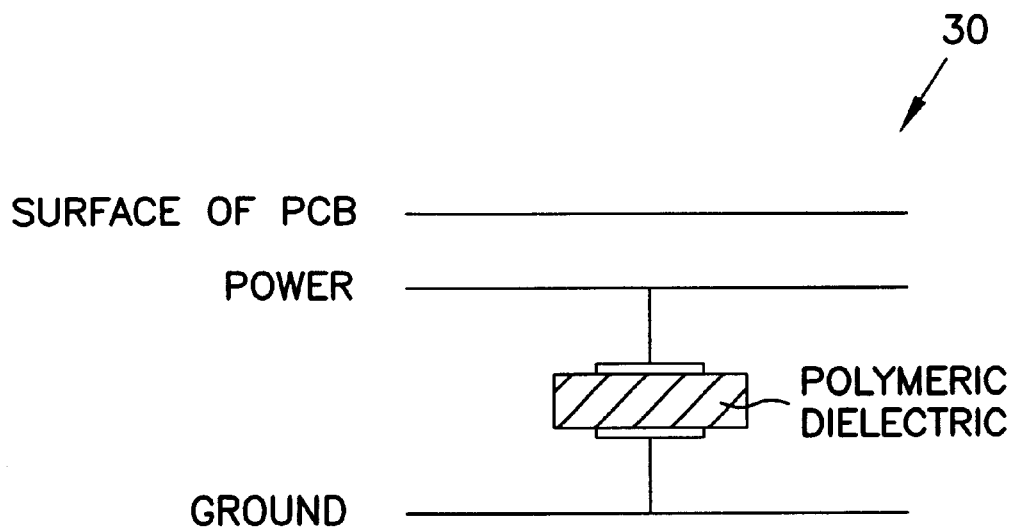
FIG. 3 illustrates a schematic view of an embedded capacitor design buried within a PCB.

It is believed that the dielectrics of the present invention are usable in processors requiring low inductance, and high capacitance in a substrate in order to reduce voltage droop. Specifically, the polymer dielectrics of the present invention have use in embedded capacitors, such as are illustrated at 10 in FIG. 3. It is believed that embedded capacitors have a potential to overcome limitations of discrete devices. Embedded capacitors have been used in PCB design, but materials of construction have not had sufficient capacitance to meet the inrush current demands for contemporary generations of IC packages. Development of high dielectric ceramics and polymer/ceramic blends for embedded capacitors is not believed to be optimal because these materials are difficult to apply and process when compared to an all polymeric dielectric of the present invention.

A low noise, high thermal dissipation polymeric dielectric material and decoupling capacitor made with the material are described herein. In the following description, numerous specific details such as material compositions, electrical component values, package designs and so forth are set forth in order to provide a more thorough understanding of the present invention. A package design refers to integrated circuits that are housed within a package that is mounted to a printed circuit board. However, it will be apparent to one skilled in the art that the present invention may be practiced without employing these specific details. In other instances, well known process techniques, and structures have not been described in detail in order to avoid unnecessarily obscuring the present invention. For instance, the capacitor described herein is usable in multi-chip modules (MCM), circuit boards, or other structures that require a capacitor in close proximity to circuitry.

Figure 5A:
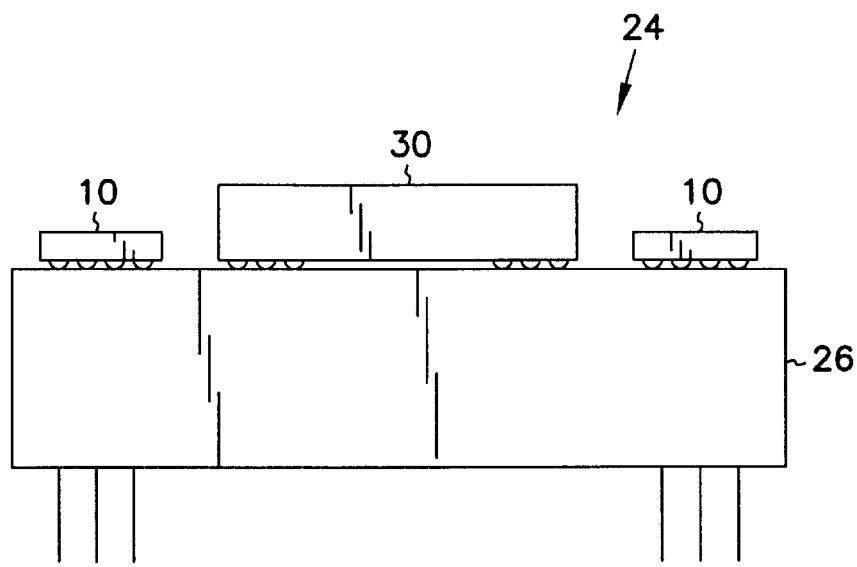
FIG. 5A illustrates a side view of a semiconductor package with capacitors mounted on a surface of the package substrate.
Figure 5B:
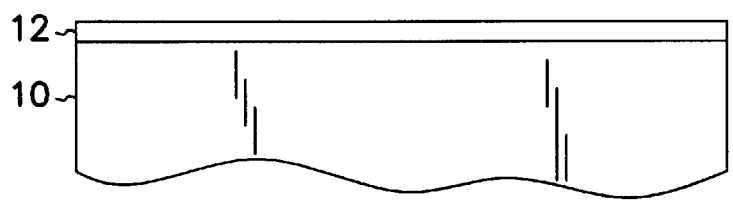
FIG. 5B illustrates a side view of a capacitor with one metal layer deposited.

While diagrams representing the present invention are illustrated in FIGS. 5A to 5B, these illustrations are not intended to limit the invention. The specific structures described herein are only meant to help clarify an understanding of the present invention and to illustrate a particular embodiment in which the present invention may be implemented. The polymeric dielectrics of the present invention are usable to make many types of discrete and embedded capacitors.

Figure 5C:
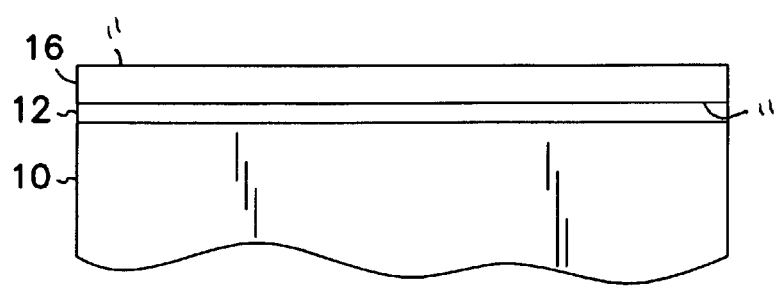
FIG. 5C illustrates the capacitor of FIG. 5B after the dielectric layer of the present invention has been deposited.
Figure 5D:
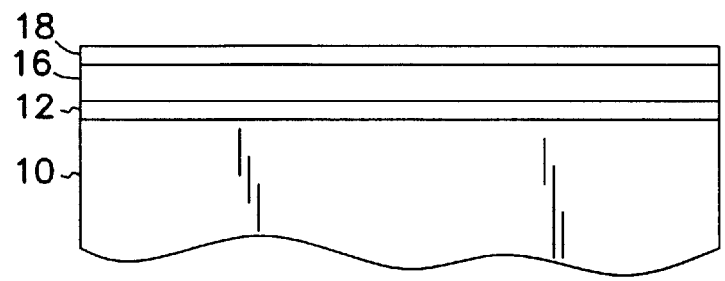
FIG. 5D illustrates the capacitor illustrated in FIG. 5C with a metal layer overlayed on the dielectric layer.
Figure 5E:
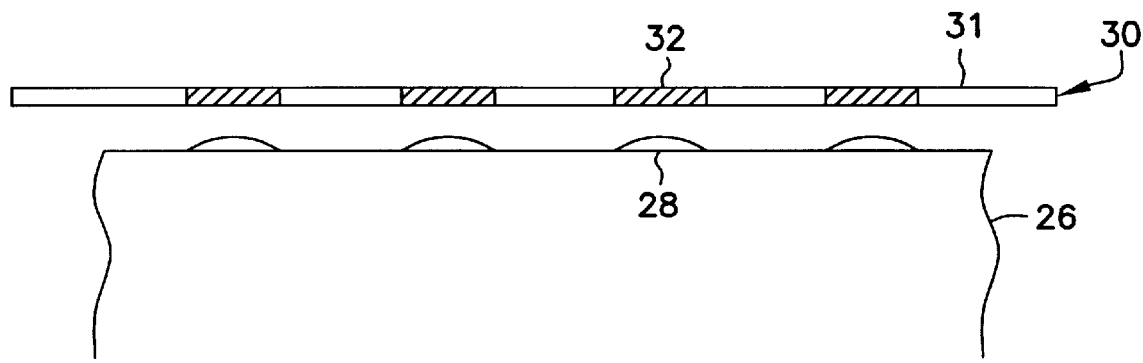
FIG. 5E illustrates a semiconductor package, electrical contact pad, and screen mesh apparatus of one embodiment of the present invention before solder paste is applied over the electrical contact pads.

Referring to FIGS. 5A–5D, a capacitor 10 having electrodes 12 and 18 is shown. The capacitor 10 comprises a combination of metal and dielectric layers, wherein the dielectric material is the dielectric of the present invention. The electrode layers 12 and 18 are separated by the dielectric layer 16, as shown in FIG. 5D. Electrodes 12 and 18 are provided at surfaces 11 of the dielectric layer 16 of capacitor 10 for electrically coupling the capacitor to other electrical devices.

Discrete capacitors such as decoupling capacitors are frequently mounted onto the substrate of a semiconductor package where they are electrically coupled to an IC device. FIG. 5A illustrates a side view of a typical semiconductor package 24 having capacitors 10 mounted on package substrate 26. Package substrate 26 contains electrical interconnects that electrically couple the IC device 30 to electrical contact pads located on the surface of the substrate. Package substrate 26 is made of any temperature resistant material, such as alumina oxide, high temperature PCB and so on in order to prevent the substrate from melting during normal reflow conditions. The electrical contact pads are comprised of an electrically conductive material, such as, for example, gold plated nickel.

The surface mounted capacitor 10 is, for some embodiments, coupled to the package with a process that relies upon evaporators to form the metallurgy necessary for electrically and mechanically coupling the capacitor. Other processes usable in the present invention include electroless and electrolytic plating processes. In another embodiment, a sputter deposition chamber is used to form a metal coating over the capacitor electrodes. Also, solder is screen printed directly onto electrical contact pads of the package substrate.

Figure 5F:
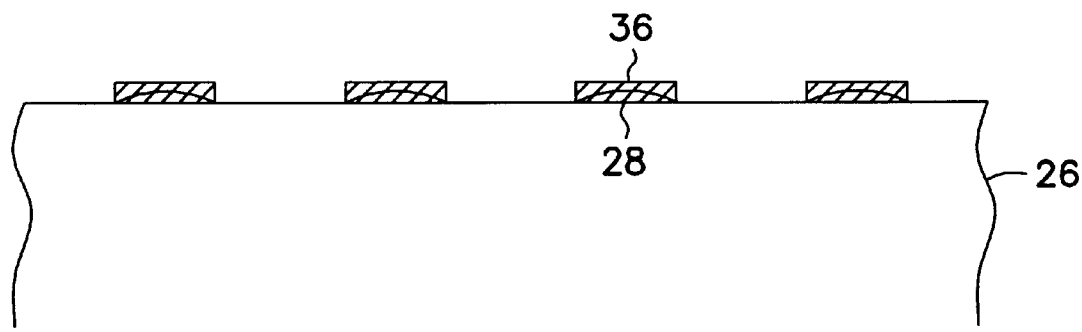
FIG. 5F illustrates the semiconductor package illustrated in FIG. 5E after solder paste is applied over the electrical contact pads.

FIG. 5B shows a side view of capacitor substrate 10 with a ground electrode 12 deposited on the substrate 10. As depicted in FIGS. 5C and 5D, a dielectric layer of the present invention 16 is disposed on the ground electrode 12. A power electrode 18 is positioned on the dielectric layer 16. Either concurrent with the formation of electrode layers 12 and 18, or at some other time, solder paste is applied over electrical contact pads 28 of package substrate 26, as shown in FIG. SE. FIG. 5F shows a cross-sectional view of the substrate 26, after solder 36 has been applied to electrical contact pads 28.

Figure 5G:
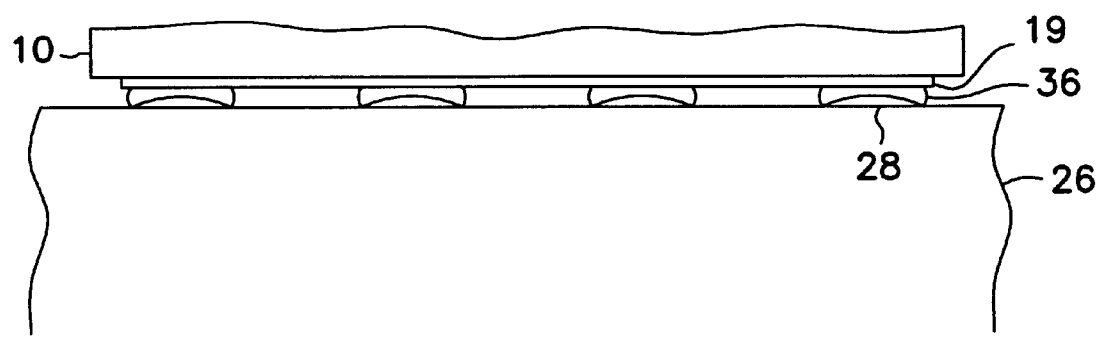
FIG. 5G illustrates the capacitor and package substrate configuration prior to reflow.

The connection between capacitor 10 and package substrate 26 is performed by positioning the metal coated regions of capacitor 10 over electrical contact pads 28 of package substrate 26, as illustrated in FIG. 5G and running the unit through a nitrogen ambient reflow furnace. The package with the capacitor is attachable to a printed circuit board using a method such as surface-mounted soldering, through-hole soldering, wire bonding or tape automated bonding.

It is believed that the dielectrics of the present invention are usable in fabrication of printed thick film capacitors and printed thin film capacitors. Printed thick film capacitive elements are formed by first depositing a base electrode, then depositing a dielectric film of the present invention. Next, a counter electrode is deposited and connection is made to a conductor pattern of the printed circuit. Printed capacitors are also fabricated by screening electrodes with a high dielectric constant material of the present invention.

In one embodiment, thin-film capacitors are vacuum deposited by using masks. In another embodiment, the thin-film capacitors are screen printed. In other embodiments, the thin-film capacitors are cast laminated by hot press or vacuum lamination. Processes of fabricating and adjusting thin-film capacitors are substantially the same as is used for thick-film capacitors.

Figure 6:
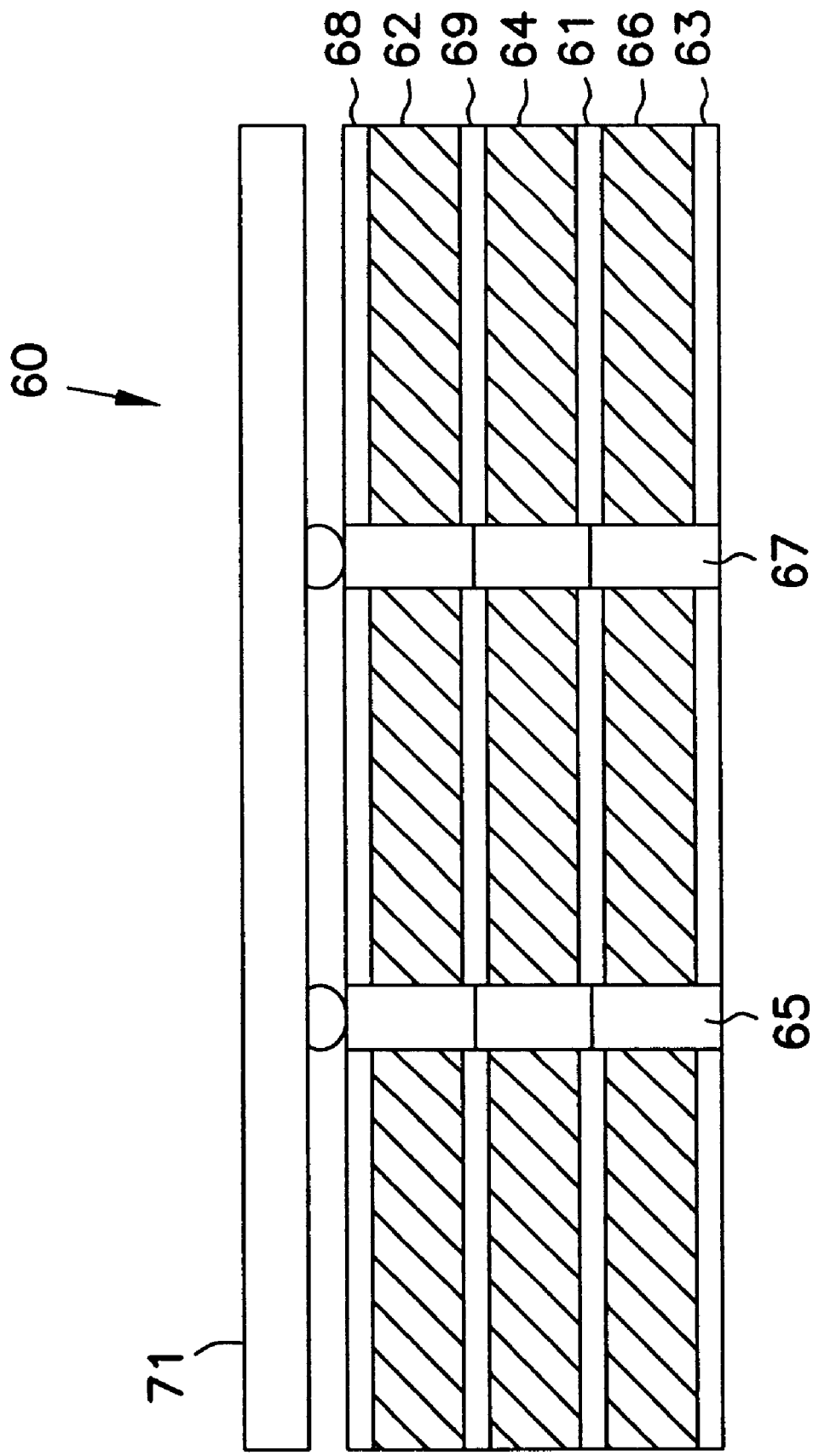
FIG. 6 illustrates a cross-sectional view of a multilayer high energy capacitor with a high dielectric polymeric material separating power and ground lines.
Figure 7:
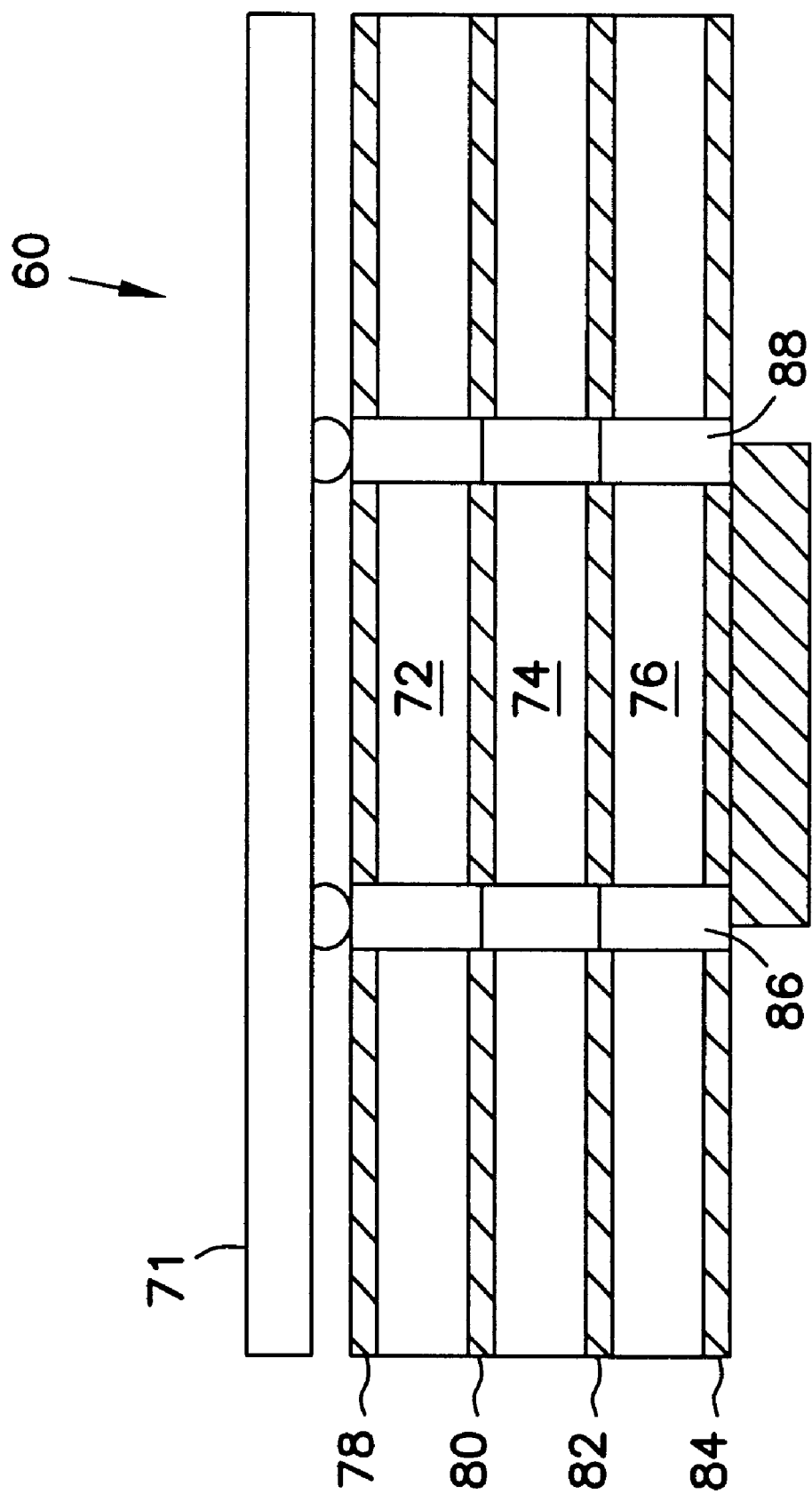
FIG. 7 illustrates a cross-sectional view of a high energy embedded capacitor fabricated with the high dielectric polymeric material of the present invention.

The present invention also includes multilayer capacitors such as are illustrated at 60 in FIG. 6 and 70 in FIG. 7. The multilayer capacitor 60 comprises layers of a high energy density dielectric of the present invention 62, 64 and 66 that are separated by power and ground lines 61, 63, 68, and 69. The multilayer capacitor 60 defines stacked, filled microvia 65 and 67. The multilayer capacitor 60 underlies a microprocessor 71.

The multilayer capacitor 70 includes the dielectric of the present invention, comprising layers 72, 74 and 76 separated by dielectric insulator layers 78, 80, 82 and 84. The capacitor 70 is positioned between vias 86 and 88. The multilayer capacitor 70 underlies the microprocessor 71.

While only certain features of the present invention have been illustrated and described herein, many modifications and changes will occur to those skilled in the art. It is, therefore, to be understood that the appended claims are intended to cover all such modifications and changes as fall within the true spirit of the invention.

What is claimed is:

1. A dielectric device, comprising:

a polymer that has a high dielectric constant, the polymer comprising polarizable species selected from the group consisting of porphyrin rings, metallophthalocyanine, ethylenediamine tetraacetate, metallocene, metallophthalocyanine, and aliphatic quaternary amines;

a base electrode over which the polymer is positioned; and a counter electrode positioned on the polymer, wherein the base electrode, polymer and counter electrode form a power conditioning capacitor.

2. The dielectric of claim 1 wherein the polarizable species comprise metal ion free dielectrics.

3. The dielectric of claim 1 wherein the polarizable species comprise metal containing dielectrics.

4. The dielectric of claim 1 wherein the polarizable species comprise complex cation containing dielectrics.

5. The dielectric of claim 1 wherein the polarizable species comprises a porphyrin ring that comprises magnesium, iron or copper chelated in the center of the ring.

6. A device comprising a metal ion or metal clusters and one or more fullerenes or nanotubes or ion exchange particles wherein the metal atoms or metal clusters are trapped in the fullerenes or nanotubes or ion exchange particles.

7. A capacitor comprising a dielectric, comprising:

a polymeric structure and a metal ion wherein the metal ion has greater motion in a vertical x—z or y—z plane than in a horizontal x—y plane;

a base electrode over which the polymer is positioned; and a counter electrode positioned on the polymer, wherein the base electrode, polymer and counter electrode form a power conditioning capacitor.

8. An electronic device, comprising a substrate, comprising a polymer that has a high dielectric constant, the polymer comprising polarizable species selected from the group consisting of porphyrin rings, metallophthalocyanine, ethylene diaminetetraacetate, metallocene, aliphatic quaternary amines, and metallophthalocyanine, a base electrode over which the polymer is positioned; and a counter electrode positioned on the polymer, wherein the base electrode, polymer and counter electrode form a power conditioning capacitor.

9. The electronic device of claim 8 wherein the substrate is formed as an article selected from the group consisting of a film, sheet, plaque, disk, laminate, or other flat shape useful in electronics.

10. The electronic device of claim 8 and further comprising one or more fullerenes or nanotubes or ion exchange particles with metal atoms or metal clusters trapped in the fullerenes or nanotubes or ion exchange particles.

11. The capacitor of claim 7 wherein the polymeric structure is a porphyrin ring.

12. The capacitor of claim 7 wherein the polymeric structure is a metallophthalocyanine.

13. The capacitor of claim 7 wherein the polymeric structure is metallocene.

14. The capacitor of claim 7 wherein the polymeric structure is an aliphatic quaternary amine.

15. An electrical device comprising the capacitor of claim 7.

\* \* \* \* \*